(12) United States Patent
Redinger et al.

(10) Patent No.: US 9,104,100 B2
(45) Date of Patent: Aug. 11, 2015

(54) PHOTORESISTS CONTAINING POLYMER-TETHERED NANOPARTICLES

(75) Inventors: David H. Redinger, Afton, MN (US); Robert J. DeVoe, Mahtomedi, MN (US); Belma Erdogan-Haug, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/007,270

(22) PCT Filed: May 23, 2012

(86) PCT No.: PCT/US2012/039081
§ 371 (c)(1),
(2), (4) Date: Sep. 24, 2013

(87) PCT Pub. No.: WO2012/170204
PCT Pub. Date: Dec. 13, 2012

(65) Prior Publication Data
US 2014/0080061 A1    Mar. 20, 2014

Related U.S. Application Data

(60) Provisional application No. 61/494,620, filed on Jun. 8, 2011.

(51) Int. Cl.
| | | |
|---|---|---|
| G03F 7/004 | (2006.01) | |
| G03F 7/20 | (2006.01) | |
| A61M 37/00 | (2006.01) | |
| G03F 7/027 | (2006.01) | |

(52) U.S. Cl.
CPC ........... *G03F 7/004* (2013.01); *A61M 37/0015* (2013.01); *G03F 7/0047* (2013.01); *G03F 7/027* (2013.01); *G03F 7/20* (2013.01); *G03F 7/70375* (2013.01); *A61M 2037/003* (2013.01); *A61M 2037/0053* (2013.01)

(58) Field of Classification Search
CPC ... G03F 7/004; G03F 7/00047; G03F 7/0037; G03F 7/2053; G03F 7/027
USPC ............ 430/270.1, 285.1, 322, 311, 331, 325
See application file for complete search history.

(56) References Cited

U.S. PATENT DOCUMENTS

| | | | |
|---|---|---|---|
| 3,018,262 A | 1/1962 | Schroeder | |
| 3,729,313 A | 4/1973 | Smith | |
| 3,741,769 A | 6/1973 | Smith | |
| 3,779,778 A | 12/1973 | Smith | |
| 3,808,006 A | 4/1974 | Smith | |
| 4,250,053 A | 2/1981 | Smith | |
| 4,279,717 A | 7/1981 | Eckberg | |
| 4,394,403 A | 7/1983 | Smith | |
| 4,491,628 A | 1/1985 | Ito | |
| 4,642,126 A | 2/1987 | Zador | |
| 4,652,274 A | 3/1987 | Boettcher | |
| 4,859,572 A | 8/1989 | Farid | |
| 5,037,579 A | 8/1991 | Matchett | |
| 5,189,136 A | 2/1993 | Wudl | |
| 5,235,015 A | 8/1993 | Ali | |
| 5,258,225 A * | 11/1993 | Katsamberis | 428/331 |
| 5,545,676 A | 8/1996 | Palazzotto | |
| 5,750,258 A * | 5/1998 | Sakai et al. | 428/405 |
| 5,753,346 A | 5/1998 | Leir | |
| 5,770,737 A | 6/1998 | Reinhardt | |
| 5,856,373 A | 1/1999 | Kaisaki | |
| 5,859,251 A | 1/1999 | Reinhardt | |
| 5,998,495 A | 12/1999 | Oxman | |
| 6,025,406 A | 2/2000 | Oxman | |
| 6,100,405 A | 8/2000 | Reinhardt | |
| 6,267,913 B1 | 7/2001 | Marder | |
| 6,334,856 B1 * | 1/2002 | Allen et al. | 604/191 |
| 6,855,478 B2 | 2/2005 | DeVoe | |
| 7,005,229 B2 | 2/2006 | Nirmal | |
| 7,189,768 B2 | 3/2007 | Baran | |
| 7,294,449 B1 * | 11/2007 | Gudeman et al. | 430/270.1 |
| 7,381,516 B2 | 6/2008 | Arney | |

(Continued)

FOREIGN PATENT DOCUMENTS

| | | |
|---|---|---|
| WO | WO 98-21521 | 5/1998 |
| WO | WO 99-53242 | 10/1999 |
| WO | WO 00-06495 | 2/2000 |
| WO | WO 00-06622 | 2/2000 |
| WO | WO 02-072189 | 9/2002 |
| WO | WO 2005-066672 | 7/2005 |
| WO | WO 2010-065247 | 6/2010 |
| WO | WO 2011-133331 | 10/2011 |
| WO | WO 2012-145282 | 10/2012 |

OTHER PUBLICATIONS

Kim et al, "Surface Modification of silica nanoparticles by UV-induced graft polymerization of methyl methacrylate", Journal of Colloidal and Interface Science 292, pp. 93-98 (2005).*

(Continued)

*Primary Examiner* — Amanda C Walke

(74) *Attorney, Agent, or Firm* — Bradford B. Wright

(57) ABSTRACT

Compositions such as photoresists and microfabrication processes are provided that can produce high-fidelity microfabricated structures. The provided photoresists can have reduced swelling during the development phase and can give tight tolerances for products, such as microneedles, that can be used, for example, in the medical field. The provided compositions include a photoresist, a photoinitiator system dispersed in the photoresist, and a polymer-tethered nanoparticle dispersed in the photoresist. The photoresist can be a negative photoresist and the photoinitiator system can include a two-photoinitiator system. The polymer-tethered nanoparticle can include an acrylic polymer and, in some embodiments, can include poly(methyl methacrylate). The nanoparticles can include silica.

10 Claims, 1 Drawing Sheet

(56) References Cited

U.S. PATENT DOCUMENTS

| | | | |
|---|---|---|---|
| 7,655,376 | B2 | 2/2010 | Anderson |
| 7,875,415 | B2 * | 1/2011 | Meagley .................... 430/270.1 |
| 2002/0022085 | A1 * | 2/2002 | Thise et al. .................... 427/215 |
| 2005/0124712 | A1 * | 6/2005 | Anderson et al. ................. 522/1 |
| 2006/0015061 | A1 * | 1/2006 | Kuo et al. ........................ 604/47 |
| 2007/0191513 | A1 * | 8/2007 | Jenrich et al. ................. 523/443 |
| 2007/0276330 | A1 * | 11/2007 | Beck et al. .................... 604/172 |
| 2008/0139683 | A1 | 6/2008 | Flynn |
| 2008/0311488 | A1 | 12/2008 | Su |
| 2008/0319122 | A1 * | 12/2008 | Filiatrault et al. ............ 524/493 |
| 2009/0099537 | A1 | 4/2009 | DeVoe |
| 2010/0006536 | A1 * | 1/2010 | Kalvesten et al. .............. 216/11 |
| 2010/0178512 | A1 * | 7/2010 | Giesenberg et al. .......... 428/405 |
| 2011/0003946 | A1 * | 1/2011 | Schuett et al. ................ 525/476 |
| 2013/0035433 | A1 | 2/2013 | Mechernich |
| 2013/0108860 | A1 | 5/2013 | Chen |
| 2014/0022644 | A1 * | 1/2014 | Hao et al. ...................... 359/586 |

OTHER PUBLICATIONS

Allen "High Performance Acrylic Polymers for Chemically Amplified Photoresist Applications", J. Vac. Sci. Technol, Nov./Dec. 1991, vol. B 9, No. 6, pp. 3357-3361.

Allen, "193 nm Single Layer Positive Resists Building Etch Resistance Into a High Resolution Imaging System", Proc. SPIE, 1995, vol. 2438, pp. 474-485.

Bartholome, "Nitroxide-Mediated Polymerizations from Silica Nanoparticle Surfaces:"Graft from" Polymerization of Styrene Using a Triethoxysilyl-Terminated Alkoxyamine Initiator", Macromolecules, 2003, vol. 36, No. 21, pp. 7946-7952.

Beringer "Diaryliodonium Salts. IX. The Synthesis of Substituted Diphenyliodonium Salts", J. Am. Chem. Soc., Jan. 20, 1959, vol. 81,pp. 342-351.

Beyou, "Nitroxide-Mediated Polymerizations from Silica Nanoparticle Surfaces:"Graft from" Polymerization of Styrene Using a Triethoxysilyl-Terminated Alkoxyamine Initiator", Macromolecules, 2003, vol. 36, No. 21, pp. 7946-7952.

Eaton, "Dye Sensitized Photopolymerization", Advances in Photochemistry, vol. 13, 427-488 (1986).

Gurr, "Acrylic Nanocomposite Resins for Use in Stereolithography and Structural Light Modulation Based Rapid Prototyping and Rapid Manufacturing Technologies", Advanced Functional Materials, 2008, vol. 18, pp. 2390-2397.

Nanoresins Data Sheet, "High Transparency and Reduced Shrinkage", 2011, 1 page.

Pyun, "Synthesis of Nanocomposite Organic/Inorganic Hybrid Materials Using Controlled/"Living" Radical Polymerization", Chem. Mater., 2001, vol. 13, No. 10, pp. 3436-3448.

Ranjan, "Combination of Living Radical Polymerization and Click Chemistry for Surface Modification", Macromolecules, 2007, vol. 40, No. 17, pp. 6217-6223.

Shukla, "Two-Photon Lithography of Sub-Wavelength Metallic Structures in a Polymer Matrix", Advanced Materials, 2010, vol. 22, pp. 3695-3699.

Ueno, "Nanoparticle Plasmon-Assisted Two-Photon Polymerization Induced by Incoherent Excitation Source", J. Am. Chem. Soc., 2008 vol. 130, pp. 6928-6929.

Xu "Measurement of two-photon excitation cross sections of molecular fluorophores with data from 690 to 1050 nm", J. Opt. Soc. Am. B, Mar. 1996, vol. 13, No. 3, pp. 481-491.

Zhao, "Reversible Addition-Fragmentation Chain Transfer Graft Polymerization Mediated by Fumed Silica Supported Chain Transfer Agents", Macromolecules, 2007, Vo. 40, No. 25, pp. 9116-9124.

Zhou, "An Efficient Two-Photon-Generated Photoacid Applied Positive-Tone 3D Microfabrication", Science, May 10, 2002, vol. 296, pp. 1106-1109.

International Search Report for PCT International Application No. PCT/US2012/039081, Mailed on Jul. 11, 2012, 4 pages.

Co-pending U.S. Appl. No. 14/002,493, entitled "Enhanced Multi-Photon Imaging Resolution", Devoe, Robert J., filed Apr. 17, 2012.

* cited by examiner

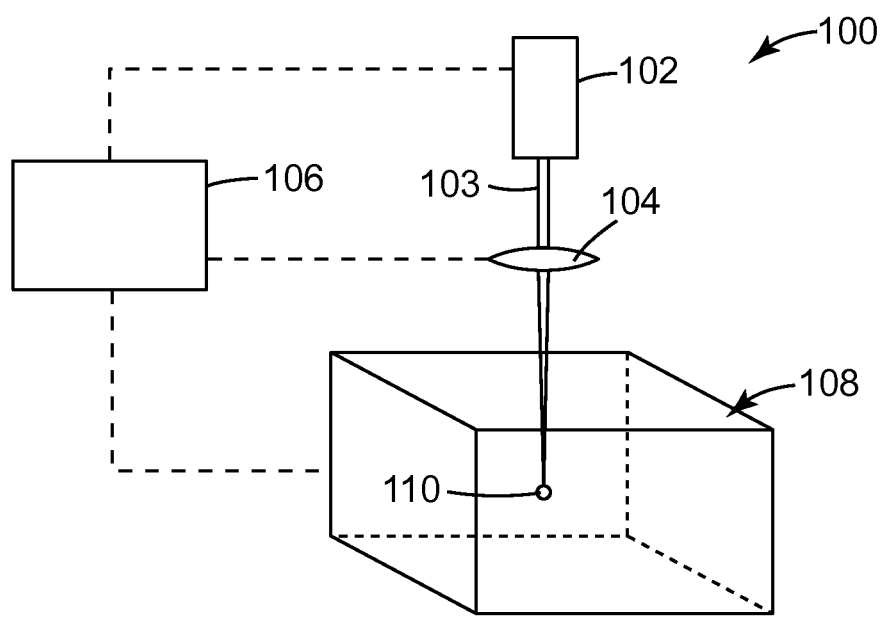

PHOTORESISTS CONTAINING POLYMER-TETHERED NANOPARTICLES

FIELD

The present disclosure generally relates to photoresists that can be useful for microfabrication.

BACKGROUND

Three-dimensional articles can be replicated from a master that can be used to fabricate a tool for microreplication. A number of technologies have been developed to make tools or molds for microreplication or nanoreplication of three-dimensional articles. These technologies include conventional photolithography and two-photon photolithography. Additionally, three-dimensional articles can be fabricated using a nonlinear thermal polymerization process.

Some microstructures such as, for example, microneedles or microneedle arrays have features that have a high aspect ratio—that is, they have a large length or height compared to their diameter. The ability to write structures using two photon-photolithography with high aspect ratios in three dimensions requires very thick layers of photoresist—particularly if the structures need to be fabricated vertically. During the development state, where unexposed photoresist is removed to reveal the desired three-dimensional structure, the developer fluid, typically a solvent for the unexposed photoresist, can be absorbed or swelled by the exposed photoresist—particularly when the development step takes long periods of time such as hours. The formed three-dimensional structure is then dried to remove the solvent. The swelling and then shrinking due to solvent removal ultimately leads to structures with reduced fidelity to the structure that was written by the two-photon exposure.

SUMMARY

Thus, there is a need for photoresists and microfabrication processes utilizing these photoresists that will give high-fidelity microfabricated structures. There is a need for photoresists that will have reduced swelling during the development phase. And there is a need for photoresists that will give tight tolerances for products, such as microneedles, that can be used, for example, in the medical field.

In one aspect, a composition is provided that includes a photoresist, a photoinitiator system dispersed in the photoresist, and a polymer-tethered nanoparticle dispersed in the photoresist. The photoresist can be a negative photoresist and the photoinitiator system can include a two-photoinitiator system. The polymer-tethered nanoparticle can include an acrylic polymer and, in some embodiments, can include poly (methyl methacrylate). The nanoparticles can include silica.

In another aspect, a method of making an article is provided that includes providing an unexposed composition that includes a photoresist, a photoinitiator system dispersed in the photoresist, and a polymer-tethered nanoparticle dispersed in the photoresist; exposing the unexposed composition with a scanned laser beam to form exposed composition in the shape of the article; and developing the composition. The composition can be as described above. The developing step can include dissolving the unexposed composition in a solvent that does not significantly swell the exposed composition. The method can be used to make hollow microneedle or microneedle arrays.

In yet another aspect, an article is provided that includes a photopolymerized composition derived from a precursor composition comprising a photoresist; a photoinitiator system dispersed in the photoresist; and a polymer-tethered nanoparticle dispersed in the photoresist. In some embodiments, the article can include a hollow microneedle. The provided hollow microneedle can shrink less than 3% in height when saturated in cyclopentanone and then dried to remove the cyclopentanone.

In this disclosure:

"aspect ratio" refers to the longest dimension of a solid divided by the shortest dimension, for example, height divided by diameter for a cone;

"dispersed" refers to a solute that is either dissolved or mixed in a solvent;

"fidelity" and "high-fidelity" refer to the quality of high resolution wherein a replicated article has any dimension that is less than 3% different from a master article;

"negative photoresist" refers to an unpolymerized or uncured polymer system that crosslinks or cures upon exposure to radiation;

"nonlinear" refers to a process in which the absorption of actinic radiation is intensity or fluence dependent;

"photoresist" refers to a polymer system that changes physical state upon exposure to radiation;

"polymer-tethered" refers to a bond between a polymer and another species such as a nanoparticle; the bond may be, for example, ionic, covalent, or metallic;

"solid" refers to a composition that can resist flow enough to hold its form for a long period of time such as days, weeks, and even months; and "voxel" refers to a volume element within a three-dimensional space.

The provided compositions and methods can produce high-fidelity microfabricated structures. These structures can have reduced swelling during the development phase and can give tight tolerances for products, such as microneedles, that can be used, for example, in the medical field.

The above summary is not intended to describe each disclosed embodiment of every implementation of the present invention. The brief description of the drawings and the detailed description which follows more particularly exemplify illustrative embodiments.

BRIEF DESCRIPTION OF THE DRAWINGS

FIG. 1 schematically illustrates one methodology for producing three-dimensional articles.

DETAILED DESCRIPTION

In the following description, reference is made to the accompanying set of drawings that form a part of the description hereof and in which are shown by way of illustration several specific embodiments. It is to be understood that other embodiments are contemplated and may be made without departing from the scope or spirit of the present invention. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

In one aspect, a composition is provided that includes a photoresist, a photoinitiator system dispersed in the photoresist, and a polymer-tethered nanoparticle also dispersed in the photoresist. The photoresist can be a positive or a negative photoresist. A positive photoresist is a type of photoresist in which the portion of the photoresist that is exposed to light becomes soluble in the photoresist developer. A negative photoresist is a type of photoresist in which the portion of the photoresist that is exposed to light becomes insoluble in the photoresist developer and the unexposed portion is dissolved by the photoresist developer. Typically, for microfabrication using photolithography, negative photoresists are employed.

The provided photoresists include both curable and non-curable species. Curable species include, for example, addition-polymerizable monomers and oligomers and addition-crosslinkable polymers (such as free-radically polymerizable or crosslinkable ethylenically-unsaturated species including, for example, acrylates, methacrylates, and certain vinyl compounds such as styrenes), as well as cationically-polymerizable monomers and oligomers and cationically-crosslinkable polymers (which species are most commonly acid-initiated and which include, for example, epoxies, vinyl ethers, cyanate esters, etc.), and mixtures thereof.

Suitable ethylenically-unsaturated species are described, for example, in U.S. Pat. No. 5,545,676 (Palazzotto et al.) and include mono-, di-, and poly-acrylates and methacrylates (for example, methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p-propoxyphenyldimethylmethane, trishydroxyethyl-isocyanurate trimethacrylate, the bis-acrylates and bis-methacrylates of polyethylene glycols of molecular weight about 200-500, copolymerizable mixtures of acrylated monomers such as those of U.S. Pat. No. 4,652,274 (Boettcher et al.), and acrylated oligomers such as those of U.S. Pat. No. 4,642,126 (Zador et al.)); unsaturated amides (for example, methylene bis-acrylamide, methylene bis-methacrylamide, 1,6-hexamethylene bis-acrylamide, diethylene triamine tris-acrylamide and beta-methacrylaminoethyl methacrylate); vinyl compounds (for example, styrene, diallyl phthalate, divinyl succinate, divinyl adipate, and divinyl phthalate); and the like; and mixtures thereof. Suitable reactive polymers include polymers with pendant (meth) acrylate groups, for example, having from 1 to about 50 (meth)acrylate groups per polymer chain. Examples of such polymers include aromatic acid (meth)acrylate half ester resins such as SARBOX resins available from Sartomer (for example, SARBOX 400, 401, 402, 404, and 405). Other useful reactive polymers curable by free radical chemistry include those polymers that have a hydrocarbyl backbone and pendant peptide groups with free-radically polymerizable functionality attached thereto, such as those described in U.S. Pat. No. 5,235,015 (Ali et al.). Mixtures of two or more monomers, oligomers, and/or reactive polymers can be used if desired. Preferred ethylenically-unsaturated species include acrylates, aromatic acid (meth)acrylate half ester resins, and polymers that have a hydrocarbyl backbone and pendant peptide groups with free-radically polymerizable functionality attached thereto.

Suitable cationically-reactive species are described, for example, in U.S. Pat. Nos. 5,998,495 and 6,025,406 (both Oxman et al.) and include epoxy resins. Such materials, broadly called epoxides, include monomeric epoxy compounds and epoxides of the polymeric type and can be aliphatic, alicyclic, aromatic, or heterocyclic. These materials generally have, on the average, at least 1 polymerizable epoxy group per molecule (preferably, at least about 1.5 and, more preferably, at least about 2). The polymeric epoxides include linear polymers having terminal epoxy groups (for example, a diglycidyl ether of a polyoxyalkylene glycol), polymers having skeletal oxirane units (for example, polybutadiene polyepoxide), and polymers having pendant epoxy groups (for example, a glycidyl methacrylate polymer or copolymer). The epoxides can be pure compounds or can be mixtures of compounds containing one, two, or more epoxy groups per molecule. These epoxy-containing materials can vary greatly in the nature of their backbone and substituent groups. For example, the backbone can be of any type and substituent groups thereon can be any group that does not substantially interfere with cationic cure at room temperature. Illustrative of permissible substituent groups include halogens, ester groups, ethers, sulfonate groups, siloxane groups, nitro groups, phosphate groups, and the like. The molecular weight of the epoxy-containing materials can vary from about 58 to about 100,000 or more.

Other epoxy-containing materials that are useful include glycidyl ether monomers of the formula

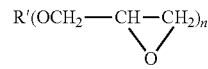

where R' is alkyl or aryl and n is an integer of 1 to 8. Examples are glycidyl ethers of polyhydric phenols obtained by reacting a polyhydric phenol with an excess of a chlorohydrin such as epichlorohydrin (for example, the diglycidyl ether of 2,2-bis-(2,3-epoxypropoxyphenol)-propane). Additional examples of epoxides of this type are described in U.S. Pat. No. 3,018,262 (Shroeder), and in *Handbook of Epoxy Resins*, Lee and Neville, McGraw-Hill Book Co., New York (1967).

A number of commercially available epoxy monomers or resins can be used. Epoxies that are readily available include, but are not limited to, octadecylene oxide; epichlorohydrin; styrene oxide; vinylcyclohexene oxide; glycidol; glycidyl methacrylate; diglycidyl ethers of bisphenol A (for example, those available as "EPON 815C", "EPON 813", "EPON 828", "EPON 1004F", and "EPON 1001F" from Hexion Specialty Chemicals, Inc., Columbus, Ohio); and diglycidyl ether of bisphenol F (for example, those available as "ARALDITE GY281" from Ciba Specialty Chemicals Holding Company, Basel, Switzerland, and "EPON 862" from Hexion Specialty Chemicals, Inc.). Other aromatic epoxy resins include the SU-8 resins available from MicroChem Corp., Newton, Mass.

Other exemplary epoxy monomers include vinyl cyclohexene dioxide (available from SPI Supplies, West Chester, Pa.); 4-vinyl-1-cylcohexene diepoxide (available from Aldrich Chemical Co., Milwaukee, Wis.); 3,4-epoxycyclohexylmethyl-3,4-epoxycyclohexene carboxylate (for example, one available as "CYRACURE UVR-6110" from Dow Chemical Co., Midland, Mich.); 3,4-epoxy-6-methylcylcohexylmethyl-3,4-epoxy-6-methyl-cylcohexane carboxylate; 2-(3,4- epoxycyclohexyl-5,5-spiro-3,4-epoxy)cyclohexane-meta-dioxane; bis(3,4-epoxycyclohexylmethyl) adipate (for example, one available as "CYRACURE UVR-6128" from Dow Chemical Co.); bis(3,4-epoxy-6-methylclyclohexylmethyl)adipate; 3,4-epoxy-6-methylcyclohexane carboxylate; and dipentene dioxide.

Still other exemplary epoxy resins include epoxidized polybutadiene (for example, one available as "POLY BD 605E" from Sartomer Co., Inc., Exton, Pa.); epoxy silanes (for example, 3,4-epoxycylclohexylethyltrimethoxysilane and 3-glycidoxypropyltrimethoxysilane, commercially available from Aldrich Chemical Co., Milwaukee, Wis.); flame retardant epoxy monomers (for example, one available as "DER-542", a brominated bisphenol type epoxy monomer available from Dow Chemical Co., Midland, Mich.); 1,4-butanediol diglycidyl ether (for example, one available as "ARALDITE RD-2" from Ciba Specialty Chemicals); hydrogenated bisphenol A-epichlorohydrin based epoxy monomers (for example, one available as "EPONEX 1510" from Hexion Specialty Chemicals, Inc.); polyglycidyl ether of phenol-formaldehyde novolak (for example, one available as "DEN-431" and "DEN-438" from Dow Chemical Co.); and epoxidized vegetable oils such as epoxidized linseed and soybean oils available as "VIKOLOX" and "VIKOFLEX" from Atofina Chemicals (Philadelphia, Pa.).

Additional suitable epoxy resins include alkyl glycidyl ethers commercially available from Hexion Specialty Chemicals, Inc. (Columbus, Ohio) as "HELOXY". Exemplary monomers include "HELOXY MODFIER 7" (a $C_8$-$C_{10}$ alky glycidyl ether), "HELOXY MODIFIER 8" (a $C_{12}$-$C_{14}$ alkyl glycidyl ether), "HELOXY MODIFIER 61" (butyl glycidyl ether), "HELOXY MODIFER 62" (cresyl glycidyl ether), "HELOXY MODIFER 65" (p-tert-butylphenyl glycidyl ether), "HELOXY MODIFER 67" (diglycidyl ether of 1,4-butanediol), "HELOXY 68" (diglycidyl ether of neopentyl glycol), "HELOXY MODIFER 107" (diglycidyl ether of cyclohexanedimethanol), "HELOXY MODIFER 44" (trimethylol ethane triglycidyl ether), "HELOXY MODIFIER 48" (trimethylol propane triglycidyl ether), "HELOXY MODIFER 84" (polyglycidyl ether of an aliphatic polyol), and "HELOXY MODIFER 32" (polyglycol diepoxide).

Other useful epoxy resins comprise copolymers of acrylic acid esters of glycidol (such as glycidyl acrylate and glycidyl methacrylate) with one or more copolymerizable vinyl compounds. Examples of such copolymers are 1:1 styrene-glycidyl methacrylate and 1:1 methyl methacrylate-glycidyl acrylate. Other useful epoxy resins are well known and contain such epoxides as epichlorohydrins, alkylene oxides (for example, propylene oxide), styrene oxide, alkenyl oxides (for example, butadiene oxide), and glycidyl esters (for example, ethyl glycidate).

Useful epoxy-functional polymers include epoxy-functional silicones such as those described in U.S. Pat. No. 4,279,717 (Eckberg et al.), which are commercially available from the General Electric Company. These are polydimethylsiloxanes in which 1-20 mole % of the silicon atoms have been substituted with epoxyalkyl groups, such as epoxy cyclohexylethyl, as described in U.S. Pat. No. 5,753,346 (Leir et al.).

Blends of various epoxy-containing materials can also be utilized. Such blends can comprise two or more weight average molecular weight distributions of epoxy-containing compounds (such as low molecular weight (below 200), intermediate molecular weight (about 200 to 1000), and higher molecular weight (above about 1000)). Alternatively or additionally, the epoxy resin can contain a blend of epoxy-containing materials having different chemical natures (such as aliphatic and aromatic) or functionalities (such as polar and non-polar). Other cationically-reactive polymers (such as vinyl ethers and the like) can additionally be incorporated, if desired. Epoxies also include aromatic glycidyl epoxies (for example, the EPON resins available from Hexion Specialty Chemicals, Inc. and the SU-8 resins available from MicroChem Corp., Newton, Mass.), and mixtures thereof.

Suitable cationically-reactive species also include vinyl ether monomers, oligomers, and reactive polymers (for example, methyl vinyl ether, ethyl vinyl ether, tert-butyl vinyl ether, isobutyl vinyl ether, triethyleneglycol divinyl ether (RAPI-CURE DVE-3, available from International Specialty Products, Wayne, N.J.), trimethylolpropane trivinyl ether, and the VECTOMER divinyl ether resins from Morflex, Inc., Greensboro, N.C. (for example, VECTOMER 1312, VECTOMER 4010, VECTOMER 4051, and VECTOMER 4060 and their equivalents available from other manufacturers)), and mixtures thereof. Blends (in any proportion) of one or more vinyl ether resins and/or one or more epoxy resins can also be utilized. Polyhydroxy-functional materials (such as those described, for example, in U.S. Pat. No. 5,856,373 (Kaisaki et al.)) can also be utilized in combination with epoxy- and/or vinyl ether-functional materials.

Non-curable species include, for example, reactive polymers whose solubility can be increased upon acid- or radical-induced reaction. Such reactive polymers include, for example, aqueous insoluble polymers bearing ester groups that can be converted by photogenerated acid to aqueous soluble acid groups (for example, poly(4-tert-butoxycarbonyloxystyrene). Non-curable species also include the chemically-amplified photoresists described by R. D. Allen et al. in "High Performance Acrylic Polymers for Chemically Amplified Photoresist Applications," *J. Vac. Sci. Technol. B*, 9, 3357 (1991). The chemically-amplified photoresist concept is now widely used for microchip manufacturing, especially with sub-0.5 micron (or even sub-0.2 micron) features. In such photoresist systems, catalytic species (typically, hydrogen ions) can be generated by irradiation, which induces a cascade of chemical reactions. This cascade occurs when hydrogen ions initiate reactions that generate more hydrogen ions or other acidic species, thereby amplifying reaction rate. Examples of typical acid-catalyzed chemically-amplified photoresist systems include deprotection (for example, t-butoxycarbonyloxystyrene resists as described in U.S. Pat. No. 4,491,628 (Ito et al.), tetrahydropyran (THP) methacrylate-based materials, THP-phenolic materials such as those described in U.S. Pat. No. 3,779,778 (Smith et al.), t-butyl methacrylate-based materials such as those described by R. D. Allen et al. in *Proc. SPIE* 2438, 474 (1995), and the like); depolymerization (for example, polyphthalaldehyde-based materials); and rearrangement (for example, materials based on the pinacol rearrangements).

If desired, mixtures of different types of reactive species can be utilized in the photoresist compositions. For example, mixtures of free-radically-reactive species and cationically-reactive species are also useful.

The provided compositions also include a photoinitiator system dispersed in the photoresist. The photoinitiator system can be a multiphoton photoinitiator system, as the use of such a system can enable polymerization to be confined or limited to the focal region of a focused beam of light. Such a system typically is a two- or three-component system that comprises at least one multiphoton photosensitizer, at least one photoinitiator (or electron acceptor), and, optionally, at least one electron donor. Such multi-component systems can provide enhanced sensitivity, enabling photoreaction to be effected in a shorter period of time and thereby reducing the likelihood of problems due to movement of the sample and/or one or more components of the exposure system.

Typically, the multiphoton photoinitiator system comprises photochemically effective amounts of (a) at least one multiphoton photosensitizer that is capable of simultaneously absorbing at least two photons and that, optionally but preferably, has a two-photon absorption cross-section greater than that of fluorescein; (b) optionally, at least one electron donor compound different from the multiphoton photosensitizer and capable of donating an electron to an electronic excited state of the photosensitizer; and (c) optionally, at least one photoinitiator that is capable of being photosensitized by accepting an electron from an electronic excited state of the photosensitizer, resulting in the formation of at least one free radical and/or acid.

Alternatively, the multiphoton photoinitiator system can be a one-component system that comprises at least one photoinitiator. Photoinitiators useful as one-component multi-photon photoinitiator systems include acyl phosphine oxides (for example, those sold by Ciba under the trade name IRGACURE 819, as well as 2,4,6 trimethyl benzoyl ethoxyphenyl phosphine oxide sold by BASF Corporation under the trade name LUCIRIN TPO-L) and stilbene derivatives with covalently attached sulfonium salt moieties (for example, those described by W. Zhou et al. in *Science* 296, 1106 (2002)). Other conventional ultraviolet (UV) photoinitiators such as benzil ketal can also be utilized, although their multiphoton photoinitiation sensitivities will generally be relatively low.

Multiphoton photosensitizers, electron donors, and photoinitiators (or electron acceptors) useful in two- and three-component multiphoton photoinitiator systems are described below.

Multiphoton photosensitizers suitable for use in the multiphoton photoinitiator system of the photoreactive compositions are those that are capable of simultaneously absorbing at least two photons when exposed to sufficient light. Preferably, the photosensitizers have a two-photon absorption cross-section greater than that of fluorescein (that is, greater than that of 3',6'-dihydroxyspiro[isobenzofuran-1(3H), 9'-[9H]xanthen]3-one). Generally, the cross-section can be greater than about $50 \times 10^{-50}$ $cm^4$ sec/photon, as measured by the method described by C. Xu and W. W. Webb in *J. Opt. Soc. Am. B*, 13, 481 (1996) (which is referenced by Marder and Perry et al. in PCT Publ. No. WO 98/21521).

Typically, the two-photon absorption cross-section of the photosensitizer is greater than about 1.5 times that of fluorescein (or greater than about $75 \times 10^{-50}$ $cm^4$ sec/photon, as measured by the above method); even more preferably, greater than about twice that of fluorescein (or greater than about $100 \times 10^{-50}$ $cm^4$ sec/photon); most preferably, greater than about three times that of fluorescein (or, alternatively, greater than about $150 \times 10^{-50}$ $cm^4$ sec/photon); and optimally, greater than about four times that of fluorescein (or, alternatively, greater than about $200 \times 10^{-50}$ $cm^4$ sec/photon).

Typically, the photosensitizer is soluble or highly dispersible in the reactive species (if the reactive species is liquid) or is compatible with the reactive species and with any binders (as described below) that are included in the composition. Most preferably, the photosensitizer is also capable of sensitizing 2-methyl-4,6-bis(trichloromethyl)-s-triazine under continuous irradiation in a wavelength range that overlaps the single photon absorption spectrum of the photosensitizer (single photon absorption conditions), using the test procedure described in U.S. Pat. No. 3,729,313 (Smith). A photosensitizer can also be selected based in part upon shelf stability considerations. Accordingly, selection of a particular photosensitizer can depend to some extent upon the particular reactive species utilized (as well as upon the choices of electron donor compound and/or photoinitiator).

Typical multiphoton photosensitizers include those exhibiting large multiphoton absorption cross-sections, such as RHODAMINE B (that is, N-[9-(2-carboxyphenyl)-6-(diethylamino)-3H-xanthen-3-ylidene]-N-ethylethanaminium chloride or hexafluoroantimonate) and the four classes of photosensitizers described, for example, by Marder and Perry et al. in PCT. Publ. Nos. WO 98/21521 and WO 99/53242. The four classes can be described as follows: (a) molecules in which two donors are connected to a conjugated π (pi)-electron bridge; (b) molecules in which two donors are connected to a conjugated π (pi)-electron bridge which is substituted with one or more electron accepting groups; (c) molecules in which two acceptors are connected to a conjugated π (pi)-electron bridge; and (d) molecules in which two acceptors are connected to a conjugated π (pi)-electron bridge which is substituted with one or more electron donating groups (where "bridge" means a molecular fragment that connects two or more chemical groups, "donor" means an atom or group of atoms with a low ionization potential that can be bonded to a conjugated π (pi)-electron bridge, and "acceptor" means an atom or group of atoms with a high electron affinity that can be bonded to a conjugated π (pi)-electron bridge). The four above-described classes of photosensitizers can be prepared by reacting aldehydes with ylides under standard Wittig conditions or by using the McMurray reaction, as detailed in PCT Publ. No. WO 98/21521.

The multi-photon photoinitiators can include at least one distyrylbenzene dye. Distyrylbenzene dyes are described, for example, in U.S. Pat. No. 6,267,913 (Marder et al.) as compounds capable of simultaneous two-photon absorption and higher order absorptions. Distyrylbenzene dyes of can have the following general structure (I).

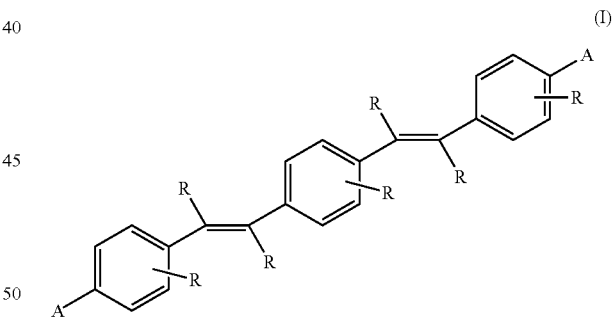

(I)

Each R can be, independently, an alkyl group, a branched alkyl group, an aromatic group, and a substituted aromatic group. In some embodiments, R groups can include alkyl groups such as methyl, ethyl, propyl, butyl, morpholino, phthalimido, and aromatic groups such as phenyl. The phenyl group may have additional substitution on the ring such as, for example, a methyl group, a methoxy group, a halogen such as fluorine, trifluoromethane, or a cyano group in one or more of the ring positions. In some embodiments, R can include H, chloro, bromo, fluoro, methoxy, ethoxy, propoxy, butoxy, or cyano. A is, independently, H, Cl, Br, $NR_3R_4$, $OR_5$, alkyl, alkenyl, aryl, and $O(C=O)R_6$, wherein $R_3$ to $R_6$ are, independently, methyl, ethyl, propyl, butyl, hydroxymethyl, hydroxyethyl, hydroxypropyl, hydroxybutyl, morphylino, phthalimido, or phenyl, and wherein the phenyl group, if present, is substituted on each ring position, independently, with H, methyl, ethyl, methoxy, ethyoxy, fluorine, trifluoromethane, or cyano. In some embodiments, the distyrylbenzene dyes can have the following structures ((II-IV)). The use of distyrylbenzene dyes as photosensitizers for enhanced image resolution has been disclosed, for example, in Applicants' copending application, U.S. Ser. No. 61/478,180, filed on Apr. 22, 2011.

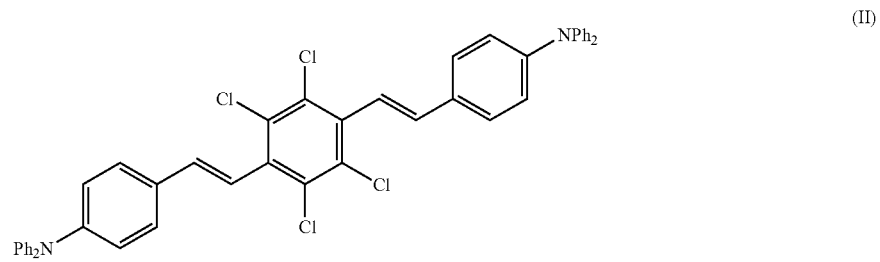

(II)

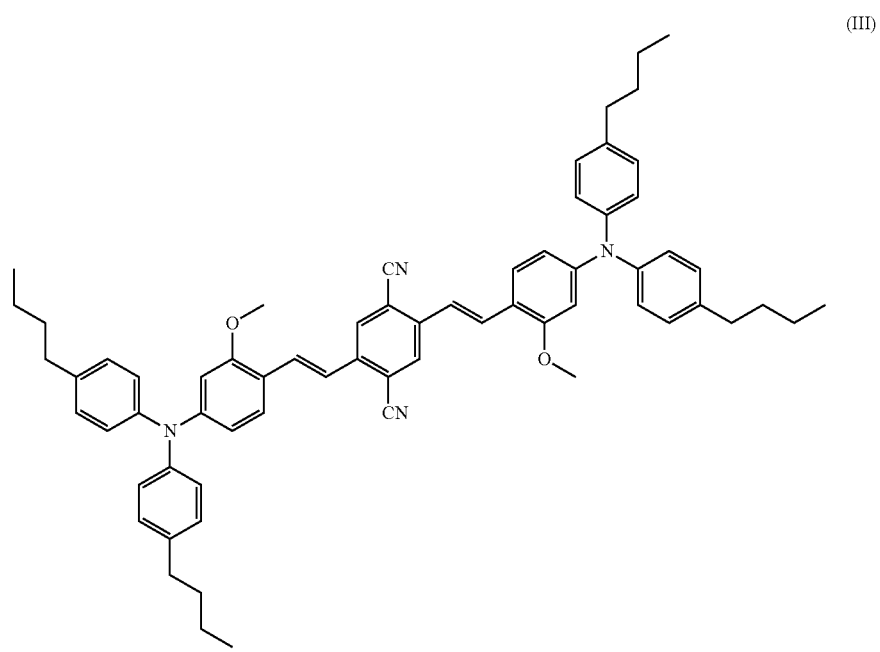

(III)

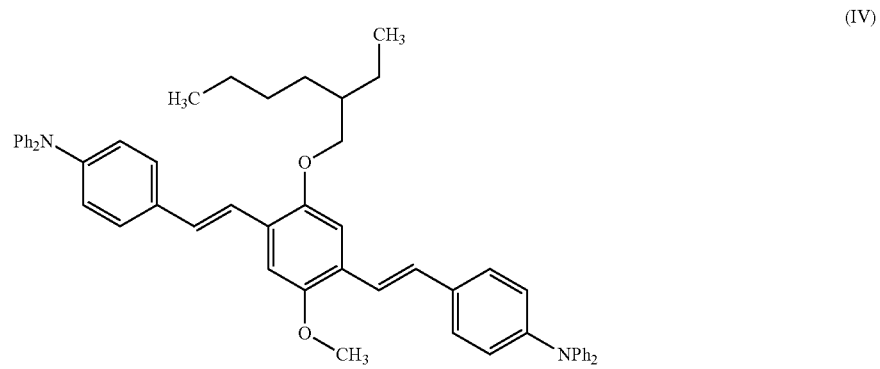

(IV)

Other compounds are depicted in Structure (V).

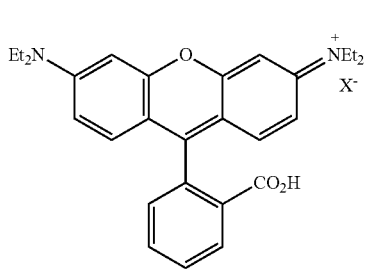

where X⁻ = Cl⁻, PF₆⁻, SbF₆⁻, AsF₆⁻,
BF₄⁻, CF₃SO₃⁻

Other useful multi-photon photosensitizer compounds are described, for example, in U.S. Pat. Nos. 6,100,405; 5,859,251; 5,770,737; and U.S. Pat. Appl. Publ. No. 2008/0139683 (all to Reinhardt et al.) as having large multi-photon absorption cross-sections, although these cross-sections were determined by a method other than that described herein. In some embodiments, the photosensitizer includes at least one chromophore having the formula:

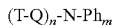

Q can be a single bond or 1,4-phenylene, n can be 1 to 3, and m has a value of (3-n). (T-Q) has the formula

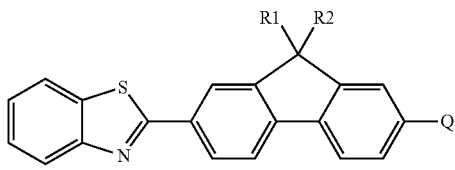

$R_1$ and $R_2$ can be alkyl groups having from 1 to 20 carbon atoms provided that when Q is a single bond, the value of n is 2 or 3. In one embodiment, the provided photosensitizer can have the following structure (Structure (VI)).

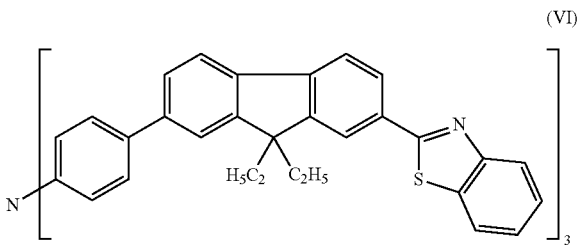

Electron donor compounds useful in the multiphoton photoinitiator system of the photoreactive compositions are those compounds (other than the photosensitizer itself) that are capable of donating an electron to an electronic excited state of the photosensitizer. Such compounds may be used, optionally, to increase the multiphoton photosensitivity of the photoinitiator system, thereby reducing the exposure required to effect photoreaction of the photoreactive composition. The electron donor compounds preferably have an oxidation potential that is greater than zero and less than or equal to that of p-dimethoxybenzene. Preferably, the oxidation potential is between about 0.3 and 1 volt vs. a standard saturated calomel electrode ("S.C.E.").

The electron donor compound is also preferably soluble in the reactive species and is selected based in part upon shelf stability considerations (as described above). Suitable donors are generally capable of increasing the speed of cure or the image density of a photoreactive composition upon exposure to light of the desired wavelength.

When working with cationically-reactive species, those skilled in the art will recognize that the electron donor compound, if of significant basicity, can adversely affect the cationic reaction (see, for example, the discussion in U.S. Pat. No. 6,025,406 (Oxman et al.).

In general, electron donor compounds suitable for use with particular photosensitizers and photoinitiators can be selected by comparing the oxidation and reduction potentials of the three components (as described, for example, in U.S. Pat. No. 4,859,572 (Farid et al.)). Such potentials can be measured experimentally (for example, by the methods described by R. J. Cox, *Photographic Sensitivity*, Chapter 15, Academic Press (1973)) or can be obtained from references such as N. L. Weinburg, Ed., *Technique of Electroorganic Synthesis Part II Techniques of Chemistry*, Vol. V (1975), and C. K. Mann and K. K. Barnes, *Electrochemical Reactions in Nonaqueous Systems* (1970). The potentials reflect relative energy relationships and can be used to guide electron donor compound selection.

If the reduction potential of the photoinitiator is less negative (or more positive) than that of the one-photon photosensitizer, an electron in the higher energy orbital of the one-photon photosensitizer is readily transferred from the one-photon photosensitizer to the lowest unoccupied molecular orbital (LUMO) of the photoinitiator, since this represents an exothermic process. Even if the process is instead slightly endothermic (that is, even if the reduction potential of the one-photon photosensitizer is up to 0.1 volt more negative than that of the photoinitiator) ambient thermal activation can readily overcome such a small barrier.

In an analogous manner, if the oxidation potential of the electron donor compound is less positive (or more negative) than that of the one-photon photosensitizer, an electron moving from the HOMO of the electron donor compound to the orbital vacancy in the one-photon photosensitizer is moving from a higher to a lower potential, which again represents an exothermic process. Even if the process is slightly endothermic (that is, even if the oxidation potential of the one-photon photosensitizer is up to 0.1 volt more positive than that of the electron donor compound), ambient thermal activation can readily overcome such a small barrier.

Slightly endothermic reactions in which the reduction potential of the one-photon photosensitizer is up to 0.1 volt more negative than that of the photoinitiator, or the oxidation potential of the one-photon photosensitizer is up to 0.1 volt more positive than that of the electron donor compound, occur in every instance, regardless of whether the photoinitiator or the electron donor compound first reacts with the one-photon photosensitizer in its excited state. When the photoinitiator or the electron donor compound is reacting with the one-photon photosensitizer in its excited state, it is preferred that the reaction be exothermic or only slightly endothermic. When the photoinitiator or the electron donor compound is reacting with the one-photon photosensitizer ion radical, exothermic reactions are still preferred, but still more endothermic reactions can be expected in many instances to occur. Thus, the reduction potential of the one-photon photosensitizer can be up to 0.2 volt (or more) more negative than that of a second-to-react photoinitiator, or the oxidation potential of the one-photon photosensitizer can be up to 0.2 volt (or more) more positive than that of a second-to-react electron donor compound.

Suitable electron donor compounds include, for example, those described by D. F. Eaton in *Advances in Photochemistry*, edited by B. Voman et al., 13, pp. 427-488, John Wiley and Sons, New York (1986); in U.S. Pat. No. 6,025,406 (Oxman et al.); and in U.S. Pat. No. 5,545,676 (Palazzotto et al.). Such electron donor compounds include amines (including triethanolamine, hydrazine, 1,4-diazabicyclo[2.2.2]octane, triphenylamine (and its triphenylphosphine and triphenylarsine analogs), aminoaldehydes, and aminosilanes), amides (including phosphoramides), ethers (including thioethers), ureas (including thioureas), sulfinic acids and their salts, salts of ferrocyanide, ascorbic acid and its salts, dithiocarbamic acid and its salts, salts of xanthates, salts of ethylene diamine tetraacetic acid, salts of $(alkyl)_p(aryl)_q$borates (p+q=4) (tetraalkylammonium salts preferred), various organometallic compounds such as $SnR_4$ compounds (where each R is independently chosen from among alkyl, aralkyl (particularly, benzyl), aryl, and alkaryl groups) (for example, such compounds as $n-C_3H_7Sn(CH_3)_3$, $(allyl)Sn(CH_3)_3$, and $(benzyl)Sn(n-C_3H_7)_3$), ferrocene, and the like, and mixtures thereof. The electron donor compound can be unsubstituted or can be substituted with one or more non-interfering substituents. Typical electron donor compounds contain an electron donor atom (such as a nitrogen, oxygen, phosphorus, or sulfur atom) and an abstractable hydrogen atom bonded to a carbon or silicon atom alpha to the electron donor atom.

Typical amine electron donor compounds include alkyl-, aryl-, alkaryl- and aralkyl-amines (for example, methylamine, ethylamine, propylamine, butylamine, triethanolamine, amylamine, hexylamine, 2,4-dimethylaniline, 2,3-dimethylaniline, o-, m- and p-toluidine, benzylamine, aminopyridine, N,N'-dimethylethylenediamine, N,N'-diethylethylenediamine, N,N'-dibenzylethylenediamine, N,N'-diethyl-1,3-propanediamine, N,N'-diethyl-2-butene-1,4-diamine, N,N'-dimethyl-1,6-hexanediamine, piperazine, 4,4'-trimethylenedipiperidine, 4,4'-ethylenedipiperidine, p-N,N-dimethyl-aminophenethanol and p-N-dimethylaminobenzonitrile); aminoaldehydes (for example, p-N,N-dimethylaminobenzaldehyde, p-N,N-diethylaminobenzaldehyde, 9-julolidine carboxaldehyde, and 4-morpholinobenzaldehyde); and aminosilanes (for example, trimethylsilylmorpholine, trimethylsilylpiperidine, bis(dimethylamino)diphenylsilane, tris(dimethylamino)methylsilane, N,N-diethylaminotrimethylsilane, tris(dimethylamino)phenylsilane, tris(methylsilyl)amine, tris(dimethylsilyl)amine, bis(dimethylsilyl)amine, N,N-bis(dimethylsilyl)aniline, N-phenyl-N-dimethylsilylaniline, and N,N-dimethyl-N-dimethylsilylamine); and mixtures thereof. Tertiary aromatic alkylamines, particularly those having at least one electron-withdrawing group on the aromatic ring, have been found to provide especially good shelf stability. Good shelf stability has also been obtained using amines that are solids at room temperature. Good photosensitivity has been obtained using amines that contain one or more julolidinyl moieties.

Typical amide electron donor compounds include N,N-dimethylacetamide, N,N-diethylacetamide, N-methyl-N-phenylacetamide, hexamethylphosphoramide, hexaethylphosphoramide, hexapropylphosphoramide, trimorpholinophosphine oxide, tripiperidinophosphine oxide, and mixtures thereof.

Typical alkylarylborate salts include: $Ar_3B(n-C_4H_9)^- N(C_2H_5)_4^+$, $Ar_3B(n-C_4H_9)^- N(CH_3)_4^+$, $Ar_3B(n-C_4H_9)^- N(n-C_4H_9)_4^+$, $Ar_3B(n-C_4H_9)^- Li^+$, $Ar_3B(n-C_4H_9)^- N(C_6H_{13})_4^+$, $Ar_3B(C_4H_9)^- N(CH_3)_3(CH_2)_2CO_2(CH_2)_2CH_3^+$, $Ar_3B(C_4H_9)^- N(CH_3)_3(CH_2)_2OCO(CH_2)_2CH_3^+$, $Ar_3B(sec-C_4H_9) CH_3)_3(CH_2)_2CO_2(CH_2)_2CH_3^+$, $Ar_3B(sec-C_4H_9)^- N(C_6H_{13})_4^+$, $Ar_3B(C_4H_9)^- N(C_8H_{17})_4^+$, $Ar_3B(C_4H_9)^- N(CH_3)_4^+$, $(p-CH_3O-C_6H_4)^-$, $Ar_3B(n-C_4H_9)^- N(n-C_4H_9)_4^+$, $Ar_3B(C_4H_9)^- N(CH_3)_3(CH_2)_2OH^+$, $Ar_3B(n-C_4H_9)_3^- N(CH_3)_4^+$, $Ar_3B(C_2H_5)_3^- N(CH_3)_4^+$, $Ar_2B(n-C_4H_9)_2^- N(CH_3)_4^+$, $Ar_3B(C_4H_9)^- N(C_4H_9)_4^+$, $Ar_4B^- N(C_4H_9)_4^+$, $ArB(CH_3)_3^- N(CH_3)_4^+$, $(n-C_4H_9)_4B^- N(CH_3)_4^+$, and $Ar_3B(C_4H_9)^- P(C_4H_9)_4^+$ (where Ar is phenyl, naphthyl, substituted (preferably, fluoro-substituted) phenyl, substituted naphthyl, and like groups having greater numbers of fused aromatic rings), as well as tetramethylammonium n-butyltriphenylborate and tetrabutylammonium n-hexyl-tris(3-fluorophenyl)borate (available as CGI 437 and CGI 746 from Ciba Specialty Chemicals Corporation, Tarrytown, N.Y.), and mixtures thereof.

Suitable ether electron donor compounds include 4,4'-dimethoxybiphenyl, 1,2,4-trimethoxybenzene, 1,2,4,5-tetramethoxybenzene, and the like, and mixtures thereof. Suitable urea electron donor compounds include N,N'-dimethylurea, N,N-dimethylurea, N,N'-diphenylurea, tetramethylthiourea, tetraethylthiourea, tetra-n-butylthiourea, N,N-di-n-butylthiourea, N,N'-di-n-butylthiourea, N,N-diphenylthiourea, N,N'-diphenyl-N,N'-diethylthiourea, and mixtures thereof.

Typical electron donor compounds for free radical-induced reactions include amines that contain one or more julolidinyl moieties, alkylarylborate salts, and salts of aromatic sulfinic acids. However, for such reactions, the electron donor compound can also be omitted, if desired (for example, to improve the shelf stability of the photoreactive composition or to modify resolution, contrast, and reciprocity). Preferred electron donor compounds for acid-induced reactions include 4-dimethylaminobenzoic acid, ethyl 4-dimethylaminobenzoate, 3-dimethylaminobenzoic acid, 4-dimethylaminobenzoin, 4-dimethylaminobenzaldehyde, 4-dimethylaminobenzonitrile, 4-dimethylaminophenethyl alcohol, and 1,2,4-trimethoxybenzene.

Suitable photoinitiators (that is, electron acceptor compounds) for the reactive species of the photoreactive compositions are those that are capable of being photosensitized by accepting an electron from an electronic excited state of the multiphoton photosensitizer, resulting in the formation of at least one free radical and/or acid. Such photoinitiators include iodonium salts (for example, diaryliodonium salts), sulfonium salts (for example, triarylsulfonium salts optionally substituted with alkyl or alkoxy groups, and optionally having 2,2'-oxy groups bridging adjacent aryl moieties), and the like, and mixtures thereof.

The photoinitiator is typically soluble in the reactive species and is also typically shelf-stable (that is, does not spontaneously promote reaction of the reactive species when dissolved therein in the presence of the photosensitizer and the electron donor compound). Accordingly, selection of a particular photoinitiator can depend to some extent upon the particular reactive species, photosensitizer, and electron donor compound chosen, as described above. If the reactive species is capable of undergoing an acid-initiated chemical reaction, then the photoinitiator is an onium salt (for example, an iodonium or sulfonium salt).

Suitable iodonium salts include those described in U.S. Pat. No. 5,545,676 (Palazzotto et al.). Suitable iodonium salts are also described in U.S. Pat. Nos. 3,729,313, 3,741,769, 3,808,006, 4,250,053 and 4,394,403 (all to Smith). The iodonium salt can be a simple salt (for example, containing an anion such as Cl⁻, Br⁻, I⁻ or C₄H₅SO₃⁻) or a metal complex salt (for example, containing SbF₆⁻, PF₆⁻, BF₄⁻, tetrakis(perfluorophenyl)borate, SbF₅OH⁻ or AsF₆⁻). Mixtures of iodonium salts can be used if desired.

Examples of useful aromatic iodonium complex salt photoinitiators include diphenyliodonium tetrafluoroborate; di(4-methylphenyl)iodonium tetrafluoroborate; phenyl-4-methylphenyliodonium tetrafluoroborate; di(4-heptylphenyl)iodonium tetrafluoroborate; di(3-nitrophenyl)iodonium hexafluorophosphate; di(4-chlorophenyl)iodonium hexafluorophosphate; di(naphthyl)iodonium tetrafluoroborate; di(4-trifluoromethylphenyl)iodonium tetrafluoroborate; diphenyliodonium hexafluorophosphate; di(4-methylphenyl)iodonium hexafluorophosphate; diphenyliodonium hexafluoroarsenate; di(4-phenoxyphenyl)iodonium tetrafluoroborate; phenyl-2-thienyliodonium hexafluorophosphate; 3,5-dimethylpyrazolyl-4-phenyliodonium hexafluorophosphate; diphenyliodonium hexafluoroantimonate; 2,2'-diphenyliodonium tetrafluoroborate; di(2,4-dichlorophenyl)iodonium hexafluorophosphate; di(4-bromophenyl)iodonium hexafluorophosphate; di(4-methoxyphenyl)iodonium hexafluorophosphate; di(3-carboxyphenyl)iodonium hexafluorophosphate; di(3-methoxycarbonylphenyl)iodonium hexafluorophosphate; di(3-methoxysulfonylphenyl)iodonium hexafluorophosphate; di(4-acetamidophenyl)iodonium hexafluorophosphate; di(2-benzothienyl)iodonium hexafluorophosphate; and diphenyliodonium hexafluoroantimonate; and mixtures thereof. Aromatic iodonium complex salts can be prepared by metathesis of corresponding aromatic iodonium simple salts (such as, for example, diphenyliodonium bisulfate) in accordance with the teachings of Beringer et al., *J. Am. Chem. Soc.* 81, 342 (1959).

Suitable iodonium salts include diphenyliodonium salts (such as diphenyliodonium chloride, diphenyliodonium hexafluorophosphate, and diphenyliodonium tetrafluoroborate), diaryliodonium hexafluoroantimonate (for example, SARCAT SR 1012 available from Sartomer Company), and mixtures thereof.

Useful sulfonium salts include those described in U.S. Pat. No. 4,250,053 (Smith) which can be represented by the formulas:

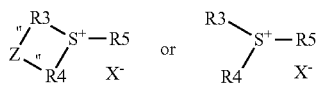

wherein R₃, R₄, and R₅ are each independently selected from aromatic groups having from about 4 to about 20 carbon atoms (for example, substituted or unsubstituted phenyl, naphthyl, thienyl, and furanyl, where substitution can be with such groups as alkoxy, alkylthio, arylthio, halogen, and so forth) and alkyl groups having from 1 to about 20 carbon atoms. As used here, the term "alkyl" includes substituted alkyl (for example, substituted with such groups as halogen, hydroxy, alkoxy, or aryl). At least one of R₃, R₄, and R₅ is aromatic, and, preferably, each is independently aromatic. Z is selected from the group consisting of a covalent bond, oxygen, sulfur, —S(=O)—, —C(=O)—, —(O=)S(=O)—, and —N(R")—, where R" is aryl (of about 6 to about 20 carbons, such as phenyl), acyl (of about 2 to about 20 carbons, such as acetyl, and benzoyl), a carbon-to-carbon bond, or —(R₆—)C(—R₇)—, where R₆ and R₇ are independently selected from the group consisting of hydrogen, alkyl groups having from 1 to about 4 carbon atoms, and alkenyl groups having from about 2 to about 4 carbon atoms.

Suitable anions, X⁻, for the sulfonium salts (and for any of the other types of photoinitiators) include a variety of anion types such as, for example, imide, methide, boron-centered, phosphorous-centered, antimony-centered, arsenic-centered, and aluminum-centered anions. Illustrative, but not limiting, examples of suitable imide and methide anions include (C₂F₅SO₂)₂N⁻, (C₄F₉SO₂)₂N⁻, (C₈F₁₇SO₂)₃C⁻, (CF₃SO₂)₃C⁻, (CF₃SO₂)₂N⁻, (C₄F₉SO₂)₃C⁻, (CF₃SO₂)₂(C₄F₉SO₂)C⁻, (CF₃SO₂)(C₄F₉SO₂)N⁻, ((CF₃)₂NC₂F₄SO₂)₂N⁻, (CF₃)₂NC₂F₄SO₂C⁻(SO₂CF₃)₂, (3,5-bis(CF₃)C₆H₃)SO₂N—SO₂CF₃, C₆H₅SO₂C⁻(SO₂CF₃)₂, C₆H₅SO₂N⁻SO₂CF₃, and the like. Typical anions of this type include those represented by the formula (R_fSO₂)₃C⁻, wherein R_f is a perfluoroalkyl radical having from 1 to about 4 carbon atoms.

Illustrative, but not limiting, examples of suitable boron-centered anions include F₄B⁻, (3,5-bis(CF₃)C₆H₃)₄B⁻, (C₆F₅)₄B⁻, (p-CF₃C₆H₄)₄B⁻, (m-CF₃C₆H₄)₄B⁻, (p-FC₆H₄)₄B⁻, (C₆F₅)₃(CH₃)B⁻, (C₆F₅)₃(n-C₄H₉)B⁻, (p-CH₃C₆H₄)₃(C₆F₅)B⁻, (C₆F₅)₃FB⁻, (C₆H₅)₃(C₆F₅)B⁻, (CH₃)₂(p-CF₃C₆H₄)₂B⁻, (C₆F₅)₃(n-C₁₈H₃₇O)B⁻, and the like. Preferred boron-centered anions generally contain 3 or more halogen-substituted aromatic hydrocarbon radicals attached to boron, with fluorine being the most preferred halogen. Illustrative, but not limiting, examples of the preferred anions include (3,5-bis(CF₃)C₆H₃)₄B⁻, (C₆F₅)₄B⁻, (C₆F₅)₃(n-C₄H₉)B⁻, (C₆F₅)₃FB⁻, and (C₆F₅)₃(CH₃)B⁻.

Suitable anions containing other metal or metalloid centers include, for example, (3,5-bis(CF₃)C₆H₃)₄Al⁻, (C₆F₅)₄Al⁻, (C₆F₅)₂F₄P⁻, (C₆F₅)F₅P⁻, F₆P⁻, (C₆F₅)F₅Sb⁻, F₆Sb⁻, (HO)F₅Sb⁻, and F₆As⁻. The foregoing lists are not intended to be exhaustive, as other useful boron-centered nonnucleophilic salts, as well as other useful anions containing other metals or metalloids, will be readily apparent (from the foregoing general formulas) to those skilled in the art. Typically the anion, X⁻, is selected from tetrafluoroborate, hexafluorophosphate, hexafluoroarsenate, hexafluoroantimonate, and hydroxypentafluoroantimonate (for example, for use with cationically-reactive species such as epoxy resins).

Examples of suitable sulfonium salt photoinitiators include: triphenylsulfonium tetrafluoroborate, methyldiphenylsulfonium tetrafluoroborate, dimethylphenylsulfonium hexafluorophosphate, triphenylsulfonium hexafluorophosphate, triphenylsulfonium hexafluoroantimonate, diphenylnaphthylsulfonium hexafluoroarsenate, tritolysulfonium hexafluorophosphate, anisyldiphenylsulfonium hexafluoroantimonate, 4-butoxyphenyldiphenylsulfonium tetrafluoroborate, 4-chlorophenyldiphenylsulfonium hexafluorophosphate, tri(4-phenoxyphenyl)sulfonium hexafluorophosphate, di(4-ethoxyphenyl)methylsulfonium hexafluoroarsenate, 4-acetonylphenyldiphenylsulfonium tetrafluoroborate, 4-thiomethoxyphenyldiphenylsulfonium hexafluorophosphate, di(methoxysulfonylphenyl)methylsulfonium hexafluoroantimonate, di(nitrophenyl)phenylsulfonium hexafluoroantimonate, di(carbomethoxyphenyl)methylsulfonium hexafluorophosphate, 4-acetamidophenyldiphenylsulfonium tetrafluoroborate, dimethylnaphthylsulfonium hexafluorophosphate, trifluoromethyldiphenylsulfonium tetrafluoroborate, p-(phenylthiophenyl)diphenylsulfonium hexafluoroantimonate, p-(phenylthiophenyl)diphenylsulfonium hexafluorophosphate, di[p-(phenylthiophenyl)]phenylsulfonium hexafluoroantimonate, di[p-(phenylthiophenyl)]phenylsulfonium hexafluorophosphate, 4,4'-bis(diphenylsulfonium)diphenylsulfide bis (hexafluoroantimonate), 4,4'-bis(diphenylsulfonium)

diphenylsulfide bis(hexafluorophosphate), 10-methylphenoxathiinium hexafluorophosphate, 5-methylthianthrenium hexafluorophosphate, 10-phenyl-9,9-dimethylthioxanthenium hexafluorophosphate, 10-phenyl-9-oxothioxanthenium tetrafluoroborate, 5-methyl-10-oxothianthrenium tetrafluoroborate, 5-methyl-10,10-dioxothianthrenium hexafluorophosphate and mixtures thereof.

Useful sulfonium salts include triaryl-substituted salts such as triarylsulfonium hexafluoroantimonate (for example, SARCAT SR1010 available from Sartomer Company), triarylsulfonium hexafluorophosphate (for example, SARCAT SR 1011 available from Sartomer Company), and triarylsulfonium hexafluorophosphate (for example, SARCAT KI85 available from Sartomer Company).

The provided prepolymer can also include an adhesion promoter. The adhesion promoter can be used to enhance the adhesion of the acrylic prepolymer to surfaces, such as glass surfaces, after polymerization. Typically, alkoxylated multifunctional monomers such as alkoxylated trifunctional acrylic esters such as SR 9008 (available from Sartomer, Exton, Pa.) can be employed as adhesion promoters in the provided acrylic photopolymer system.

The provided composition also includes at least one polymer-tethered nanoparticle dispersed in the photoresist. Typical polymer-tethered nanoparticles include a polymer that includes a functional group and nanoparticles that have been surface-modified to allow bonding to the functional group. The polymer can include acrylates such as poly(methyl methacrylate) (PMMA) and can have a molecular weight ($M_n$) of from about 9,000 to about 120,000 or from about 9,000 to about 50,000. The polymers can be provided functional groups by reaction with, for example, a silane during polymerization. In some embodiments, methyl methacrylate can be polymerized in the presence of chain transfer agents such as mercaptopropyl trimethoxysilane to give a PMMA polymer terminated with trimethoxysilane groups. These functionalized polymers can then be tethered to surface-modified nanoparticles using, for example, isooctyltrimethoxysilane. It is contemplated that the polymers in the polymer-tethered nanoparticles are made prior to tethering them to that nanoparticle. As a result they have defined molecular weight and structure and are not formed in situ.

Polymer-tethered nanoparticles contemplated by this disclosure include acrylic polymers as described above that are bonded to surface-modified nanoparticles. The nanoparticles can be inorganic. Examples of suitable inorganic nanoparticles include silica and metal oxide nanoparticles including zirconia, titania, calcium phosphate, e.g., hydroxy-apatite, ceria, alumina, iron oxide, vanadia, antimony oxide, tin oxide, alumina/silica, and combinations thereof, and include combined materials such as a mixture of materials or layers of materials surrounding a central inorganic core. The nanoparticles can have an average particle diameter less than about 100 nm, in other embodiments, no greater than about 50 nm; from about 3 nm to about 50 nm; from about 3 nm to about 20 nm; and from about 5 nm to about 10 nm. The ranges can include any size or range in between 3 nm and less than 100 nm. If the nanoparticles are aggregated, the maximum cross-sectional dimension of the aggregated particle is within any of these preferable ranges.

Useful surface-modified zirconia nanoparticles include a combination of oleic acid and acrylic acid adsorbed onto the surface of the particle. Useful surface-modified silica nanoparticles include silica nanoparticles surface-modified with silane surface modifying agents including, e.g., acryloyloxypropyl trimethoxysilane, 3-methacryloyloxypropyltrimethoxysilane, 3-mercaptopropyltrimethoxysilane, n-octyltrimethoxysilane, isooctyltrimethoxysilane, and combinations thereof. Silica nanoparticles can be treated with a number of surface modifying agents including, e.g., alcohol, organosilane including, e.g., alkyltrichlorosilanes, trialkoxyarylsilanes, trialkoxy(alkyl)silanes, and combinations thereof and organotitanates and mixtures thereof.

The nanoparticles may be in the form of a colloidal dispersion. Examples of useful commercially available unmodified silica starting materials include nano-sized colloidal silicas available under the product designations NALCO 1040, 1050, 1060, 2326, 2327, and 2329 colloidal silica from Nalco Chemical Co., Naperville, Ill. Useful metal oxide colloidal dispersions include colloidal zirconium oxide, suitable examples of which are described in U.S. Pat. No. 5,037,579 (Matchett), and colloidal titanium oxide, useful examples of which are described in PCT Publ. No. WO 00/06495 (Arney et al.)

Surface modifying groups may be derived from surface modifying agents. Schematically, surface modifying agents can be represented by the formula A-B, where the A group is capable of attaching to the surface of the particle and the B group is a compatibilizing group that may be reactive or non-reactive with a component of the continuous phase. Compatibilizing groups can be selected to render the particle relatively more polar, relatively less polar or relatively non-polar.

Suitable classes of surface-modifying agents include, e.g., silanes, organic acids organic bases and alcohols, and combinations thereof. Particularly useful surface-modifying agents include silanes. Examples of useful silanes include organosilanes including, e.g., alkylchlorosilanes, alkoxysilanes, e.g., methyltrimethoxysilane, methyltriethoxysilane, ethyltrimethoxysilane, ethyltriethoxysilane, n-propyltrimethoxysilane, n-propyltriethoxysilane, i-propyltrimethoxysilane, i-propyltriethoxysilane, butyltrimethoxysilane, butyltriethoxysilane, hexyltrimethoxysilane, octyltrimethoxysilane, 3-mercaptopropyltrimethoxysilane, n-octyltriethoxysilane, phenyltriethoxysilane, polytriethoxysilane, vinyltrimethoxysilane, vinyldimethylethoxysilane, vinylmethyldiacetoxysilane, vinylmethyldiethoxysilane, vinyltriacetoxysilane, vinyltriethoxysilane, vinyltriisopropoxysilane, vinyltrimethoxysilane, vinyltriphenoxysilane, vinyltri(t-butoxy)silane, vinyltris(isobutoxy)silane, vinyltris (isopropenoxy)silane, and vinyltris(2-methoxyethoxy)silane; trialkoxyarylsilanes; isooctyltrimethoxy-silane; N-(3-triethoxysilylpropyl) methoxyethoxyethoxy ethyl carbamate; N-(3-triethoxysilylpropyl) methoxyethoxyethoxyethyl carbamate; silane functional (meth)acrylates including, e.g., 3-(methacryloyloxy)propyltrimethoxysilane, 3-acryloyloxypropyltrimethoxysilane, 3-(methacryloyloxy) propyltriethoxysilane, 3-(methacryloyloxy)propylmethyldimethoxysilane, 3-(acryloyloxypropyl)methyldimethoxysilane, 3-(methacryloyloxy)propyldimethylethoxysilane, 3-(methacryloyloxy)methyltriethoxysilane, 3-(methacryloyloxy)methyltrimethoxysilane, 3-(methacryloyloxy)propyldimethylethoxysilane, 3-(methacryloyloxy)propenyltrimethoxysilane, and 3-(methacryloyloxy) propyltrimethoxysilane; polydialkylsiloxanes including, e.g., polydimethylsiloxane, arylsilanes including, e.g., substituted and unsubstituted arylsilanes, alkylsilanes including, e.g., substituted and unsubstituted alkyl silanes including, e.g., methoxy and hydroxy substituted alkyl silanes, and combinations thereof.

Useful organic acid surface-modifying agents include, e.g., oxyacids of carbon (e.g., carboxylic acid), sulfur and phosphorus, and combinations thereof. Representative examples of polar surface-modifying agents having carboxylic acid functionality include $CH_3O(CH_2CH_2O)_2CH_2COOH$ (hereafter MEEAA) and 2-(2-methoxyethoxy)acetic acid having the chemical structure $CH_3OCH_2CH_2OCH_2COOH$ (hereafter MEAA) and mono(polyethylene glycol) succinate in either acid or salt forms. Representative examples of nonpolar surface-modifying agents having carboxylic acid functionality include octanoic acid, dodecanoic acid and oleic acid.

Examples of suitable phosphorus containing acids include phosphonic acids including, e.g., octylphosphonic acid, laurylphosphonic acid, decylphosphonic acid, dodecylphosphonic acid, octadecylphosphonic acid, and monopolyethylene glycol phosphonate in either acid or salt forms. Useful organic base surface-modifying agents also include, e.g., alkylamines including, e.g., octylamine, decylamine, dodecylamine, octadecylamine, and monopolyethylene glycol amines.

Examples of other useful non-silane surface modifying agents include acrylic acid, methacrylic acid, beta-carboxyethyl acrylate, mono-2-(methacryloyloxyethyl) succinate, and combinations thereof. A useful surface modifying agent that imparts both polar character and reactivity to the nanoparticles is mono(methacryloyloxypolyethyleneglycol) succinate. Examples of suitable surface-modifying alcohols include, e.g., aliphatic alcohols including, e.g., octadecyl, dodecyl, lauryl and furfuryl alcohol, alicyclic alcohols including, e.g., cyclohexanol, and aromatic alcohols including, e.g., phenol and benzyl alcohol, and combinations thereof.

A variety of methods are available for modifying the surface of nanoparticles including, e.g., adding a surface modifying agent to nanoparticles (e.g., in the form of a powder or a colloidal dispersion) and allowing the surface modifying agent to react with the nanoparticles. One skilled in the art will recognize that multiple synthetic sequences to bring the nanoparticle together with the compatibilizing group are possible and are envisioned within the scope, e.g., the reactive group/linker may be reacted with the nanoparticle followed by reaction with the compatibilizing group. Alternatively, the reactive group/linker may be reacted with the compatibilizing group followed by reaction with the nanoparticle.

The provided compositions can include polymer-tethered nanoparticles in an amount of from about 10 weight percent to about 80 weight percent, from about 20 weight percent to about 60 weight percent, from about 20 weight percent to about 50 weight percent or even from about 20 weight percent to about 40 weight percent based upon the total solid weight of the composition.

The provided method includes imagewise exposing at least one or more voxels of the photocurable composition described above to a dose of electromagnetic energy under conditions that are effective to photodefineably form at least one solid (or crosslinked) voxel of a three-dimensional microstructure having a volume. The volume of the solid voxel varies inversely with the dose of electromagnetic energy. That is, after a threshold dose of electromagnetic radiation higher doses of electromagnetic radiation the solid voxel size decreases as the dose of electromagnetic energy is increased.

The photocurable composition includes a photoinitiator system capable of simultaneous absorption of at least two photons and imagewise exposing (voxel by voxel) the multi-photon-absorbing composition with light sufficient to cause the photoinitiator system to absorb at least two photons, wherein the exposure takes place in a three-dimensional pattern by stepwise exposure. One or more portions of the composition are imagewise exposed to the electromagnetic energy under conditions effective to photodefinably form at least a portion of a three-dimensional microstructure or nanostructure. Photocurable compositions that are effective to photodefineably form at least a portion of a three-dimensional microstructure and photodefinability are further described in U.S. Pat. No. 6,855,478 (DeVoe et al.).

FIG. 1 schematically illustrates one methodology for producing three-dimensional microstructures and nanostructures. Referring to FIG. 1, system 100 includes laser light source 102 that directs laser beam 103 through optical lens system 104. Optical lens system 104 focuses laser light 103 within focal region (voxel) 110 within body 108 that includes a composition that comprises a polymerizable mixture. A suitable translation mechanism, represented by 106 provides relative movement between body 108, optical lens system 104 and/or focal region 110 in three dimensions to allow the focal region to be positioned at any desired location within body 108. This relative movement can occur by physical movement of light source 102, optical lens system 104, and/or body 108, and may form one or more three-dimensional structures within body 108. One suitable translation system can include a mirror-mounted galvanometer with a moving (translation) stage.

Useful exposure systems include at least one light source (usually a pulsed laser) and at least one optical element. Typically, light sources include, for example, femtosecond near-infrared titanium sapphire oscillators (for example, a Coherent Mira Optima 900-F) pumped by an argon ion laser (for example, a Coherent Innova). This laser, operating at 76 MHz, has a pulse width of less than 200 femtoseconds, is tunable between 700 and 980 nm, and has average power up to 1.4 Watts.

Another example is a Spectra Physics "MAI TAP" Ti:sapphire laser system, operating at 80 MHz, average power about 0.85 Watts, tunable from 750 to 850 nm, with a pulse width of about 100 femtoseconds. However, in practice, any light source that provides sufficient intensity (to effect multi-photon absorption) at a wavelength appropriate for the photosensitizer (used in the photoreactive composition) can be utilized. Such wavelengths can generally be in the range of about 300 to about 1500 nm; preferably, from about 600 to about 1100 nm; more preferably, from about 750 to about 850 nm.

Q-switched Nd:YAG lasers (for example, a Spectra-Physics Quanta-Ray PRO), visible wavelength dye lasers (for example, a Spectra-Physics Sirah pumped by a Spectra-Physics Quanta-Ray PRO), and Q-switched diode pumped lasers (for example, a Spectra-Physics FCbar) also can be utilized.

One skilled in the art can choose appropriate settings for using such laser systems to carry out multi-photon polymerization. For example, pulse energy per square unit of area ($E_p$) can vary within a wide range and factors such as pulse duration, intensity, and focus can be adjusted to achieve the desired curing result in accordance with conventional practices and knowledge of the contrast curve for the specific photoresist determined experimentally. If $E_p$ is too high, the material being cured can be ablated or otherwise degraded. If $E_p$ is too low, curing may not occur or may occur too slowly.

In terms of pulse duration when using near infrared pulsed lasers, preferred a preferred pulse length is generally less than about $10^{-8}$ second, more preferably less than about $10^{-9}$ second, and most preferably less than about $10^{-11}$ second. Laser pulses in the femtosecond regime are most preferred as these provide a relatively large window for setting $E_p$ levels that are suitable for carrying out multi-photon curing. With picosecond pulses, the operational window is not as large. With nanosecond pulses, curing may proceed slower than might be desired in some instances or not at all. With such relatively long pulses, the $E_p$ level may need to be established at a low level to avoid material damage when the pulses are so long, relatively.

The provided method can further include removing material that has not been exposed to the light. The multi-photon-absorbing composition can include a curable species. That is, the photodefinable species can be a curable material. Alternatively, it can be a material that is depolymerized, for example, by absorption of the photons. Typically, the material is a curable material and removing material that has not been exposed to the light includes removing the uncured material. This removal step (developing) can occur using a variety of techniques, one of which involves dissolving uncured material in a suitable solvent. The provided method includes developing at least partially, the photodefinably formed portion of the three-dimensional microstructure.

The provided methods and compositions can be used, for example, to fabricate high-fidelity microstructures, such as microneedles. As explained above, the microstructures are formed by two-photon exposure of a photoresist composition followed by development. Development involves removing unpolymerized material from the polymerized microstructure (exposed composition) with a solvent and then drying the polymerized microstructure. As explained in the example section below, in one embodiment, articles, such as microneedles were fabricated with provided compositions which shrunk in height less than about 10 percent, less than about 5 percent, or even less than about 3 percent when dried of solvent during development. The provided method can also be used to make articles that swell less than about 10 percent, less than about 5 percent, or even less than about 3 percent in volume during development.

Objects and advantages of this invention are further illustrated by the following examples, but the particular materials and amounts thereof recited in these examples, as well as other conditions and details, should not be construed to unduly limit this invention.

EXAMPLES

Example 1

Preparation of PMMA-Tethered Nanoparticles 150 g of methyl methacrylate (Sigma-Aldrich Co., Milwaukee, Wis.) were polymerized in a glass bottle containing 0.0385 g of the thermal initiator VAZO 67 (DuPont, Wilmington, Del.), 1.667 g of the chain transfer agent mercaptopropyl trimethoxysilane (Gelest Inc., Morrisville, Pa.) and 500 ml of tetrahydrofuran (THF). Four separate polymerization reactions were conducted at the same time with the same amount of ingredients. The bottles were placed in a 70° C. water bath for 24 hrs. GPC results showed that the molecular weights of all the polymers were in the range of 27000+250 g/mol. Some of the solvent was removed at reduced pressure on a rotory evaporator and the silane functionalized polymer was used as a 32.30% solids solution in the next step.

5 nm silica nanoparticles (Nalco 2326, Nalco Company, Naperville, Ill.) were modified with different percentages of the silane functionalized poly(methyl methacrylate) (PMMA). The general procedure was as follows and the exact compositions are given in the table below. A solution of the silane functionalized pol(methyl methacrylate) in THF and isooctyltrimethoxysilane (Gelest Inc., Morrisville, Pa.) were dissolved in 1-methoxy-2-propanol and added to a stirred aqueous solution of silica nanoparticles. The mixture was heated for 24 hrs at 80° C. After the reaction, the solutions were placed in aluminum pans and completely dried in a batch oven at 120° C. Final samples were dissolved in cyclopentanone at 30-45% solids level before they were used.

TABLE 1

| Materials Used for Example 1 | |
|---|---|
| Nalco 2326 (5 nm) (16.15% aq. Sol), (g) | 25.00 |
| ~27 K/mol PMMA-Silane (g) | 53.18 |
| Amount of 27 k/mol PMMA-Silane soln (32.20% solid in THF) (g) | 164.64 |
| Isooctyltrimethoxysilane (g) | 1.83 |
| 1-Methoxy-2-Propanol (g) | 150.00 |

Example 2

Preparation of Nanoparticle Containing Resist (Solution A)

Dye 1 refers to a multiphoton sensitizing dye, bis-[4-(diphenylamino)styryl]-1-(2-ethylhexyloxy)-4-(methoxy) benzene, prepared according to the following procedure: A mixture of 2,5-bis(chloromethyl)-1-methoxy-4-(2-ethylhexyloxy)benzene (28.60 g), prepared according to the procedure of U.S. Pat. No. 5,189,136 (Wudl et al.) and triethyl phosphite (37.4 g) was heated to reflux for 4 hours. After cooling, the product was heated under high vacuum to remove residual triethyl phosphite. A thick oil was obtained which slowly crystallized after several days and was used without further purification in the following step. To a mixture of the thick oil (34.35 g), 4-diphenylaminobenzaldehyde (36.54 g), and dry tetrahydrofuran (1052.97 g) was added dropwise potassium t-butoxide (1.0 M in tetrahydrofuran, 117.52 g). The mixture was stirred for 3 hours at room temperature, then the solvent was removed under vacuum. Water (296 mL) and dichloromethane (795 g) was added to the residue, hydrochloric acid (2 g) was added to produce an acidic mixture for phase separation. The mixture was extracted two more times with dichloromethane. The combined organic layers were washed with brine, dried over anhydrous magnesium sulfate and the solvent was removed under vacuum. The crude product was purified by column chromatography on silica gel using 30/70 methylene chloride/hexane to give 36 g of bis-[4-(diphenylamino)stryl]-1-(2-ethylhexyloxy),4-(methoxy) benzene as a bright green solid The following preparation was done under red lights to prevent exposure to wavelengths shorter than approximately 575 nm. Add 1.815 g 900 k MW poly(methyl methacrylate) (Sigma-Aldrich Co., Milwaukee, Wis.), 5.49 g tris-(2-hydroxyethyl)isocyanurate triacrylate (tradename SR368 obtained from Sartomer USA, LLC, Exton, Pa.) and 3 g of PMMA-tethered nanoparticle solution from Example 1 (45.17 wt. % solids in cyclopentanone) to 6.216 g cyclopentanone and mix 4 hours. The initiator package was then added and mixed for 2 hours. The initiator package consisted of 2.36 g of the following formulation: 10 g cyclopentanone, 0.205 g Dye 1, 0.410 g SR1012 (diaryliodonium hexafluoroantimonate obtained from Sartomer USA, LLC, Exton, Pa.), and 0.1 g phenothiazine (Sigma-Aldrich Co., Milwaukee, Wis.) which had been mixed using a stir-bar for 20 minutes. In this example the nanoparticles comprised approximately 15.4 wt % of the total solids.

Comparative Example 1

Non-Nanoparticle Containing Resist (Solution B)

Prepared under red light conditions (>575 nm) an in Example 2.

To prepare, 28.89 g of 900 k MW PMMA and 32.94 g SR368 were added to 37.29 g cyclopentanone and mixed for three hours. Then 14.16 g of the following formulation was added and mixed for 20 minutes in an amber bottle: 20 g cyclopentanone, 0.2 g phenothiazine, 0.82 g SR1012, and 0.41 g Dye 1.

Example 2

Writing and Measurement of Shrinkage

Copper substrates approximately 2 inches (5 cm) in diameter were coated with a diamond-like glass film (an amorphous random covalent network comprising of carbon, hydrogen, silicon and oxygen), approximately 100 nm thick, using a Plasmatherm Batch Reactor system at a pressure of approximately 2 mT using 150 sccm of tetramethylsilane gas and a radio frequency (RF) power of 1000 W. The Plasma-Therm Batch Reactor was a commercial batch plasma system (Model 3032, Plasma-Therm, St. Petersburg, Fla.) configured for reactive ion etching (RIE) with a 26-inch lower powered electrode and central gas pumping. The chamber was pumped by a roots blower (Edwards Model EH1200) backed by a dry mechanical pump (Edwards Model iQDP80). RF power was delivered by a 5 kW, 13.56 Mhz solid-state generator (RFPP Model RF50S0) through an impedance matching network. The flow rates of the gases were controlled by MKS flow controllers. Substrates for deposition were placed on the lower powered electrode. Samples of the substrates were placed on the powered electrode of the batch plasma apparatus. The plasma treatment was performed by feeding the appropriate types of gases at the prescribed flow rates. Once the flows were stabilized, the radio-frequency (RF) power was applied to the electrode to generate the plasma. The plasma was left on for approximately 30 seconds. After the plasma treatment was completed, the gases were shut off and the chamber was vented to atmosphere and the substrates were taken out of the chamber.

A solution consisting of two weight percent 3-(trimethoxysilyl)propyl methacrylate in 190-proof ethanol that had been made acidic (pH between 4 and 5) with acetic acid was then drop-cast onto the substrate and left for 1-2 minutes. Excess solution was rinsed off using 200 proof ethanol. The substrate was then baked on a hotplate at 105° C. for 4 minutes.

Poly(methyl methacrylate), having a number average molecular weight of approximately 120,000, SR9008 (Sartomer USA, LLC, Exton, Pa.), and SR368 were combined in a weight ratio of 30:35:35 to provide a monomer mixture, and this mixture was dissolved in sufficient cyclopentanone to afford a solution that was 54 weight percent of the monomer mixture. To this mixture was added sufficient bis(2,4,6-trimethylbenzoyl)phenylphosphine oxide (available as CGI-819 from Ciba Additives, Tarrytown, N.Y.) to make the CGI-819 2.91 weight percent of the total solids content and fluorosurfactant FC-4330 (available from 3M Company, St. Paul, Minn.) such that the FC-4330 was 0.096 weight percent of the total solids content, and sufficient cyclopentanone to bring the total solids to 50.7 weight percent. Six grams of this mixture was filtered through a 0.7 micron filter and then coated onto the substrate using a spin coater, to a thickness of approximately 10 microns. After drying on a hotplate at 80° C. for 5 minutes, the monomer was cured with UV light using a D bulb.

Solution A was filtered through a 5 micron glass filter (Pall Acrodisc 32 mm syringe filter, Pall Corporation, Port Washington, N.Y.) prior to deposition. Solution B was filtered through a 0.7 micron syringe filter (Whatman 25 mm GF/F, GE, Fairfield, Conn.). A sample was prepared by pouring 5.3 g of filtered Solution A onto a copper substrate that had previously been prepared as described, forming Sample A. A second sample was prepared by pouring 6 g of filtered Solution B onto a similarly prepared copper substrate, forming Sample B. After deposition the copper substrates were put into a 60° C. oven for a minimum of 2 days to drive off solvent.

Two-Photon polymerization of the dry coating was carried out in the following manner, using a diode-pumped Ti:sapphire laser (Spectra-Physics, Mountain View, Calif.), operating at a wavelength of 800 nm, nominal pulse width of 80 fs, pulse repetition rate of 80 MHz, and average power of approximately 1 W. The coated substrate was placed on a computer-controllable three-axis stage (obtained from Aerotech, Inc., Pittsburgh, Pa.). The laser beam was attenuated and shuttered using a Pockel's cell in conjunction with a polarizing beam splitter and was focused into the coating using a galvoscanner with telescope for x, y, and z-axis control (available from Nutfield Technology, Inc., Windham, N.H.) and a lens (Nikon Fluor 20× water objective, working distance 2.0 mm, 0.5 N.A.) which was immersed in FC-70 (3M Company, St. Paul, Minn.) index matching fluid resting on top of the dried film. The average power was measured at the output of the objective lens using a wavelength-calibrated photodiode (obtained from ThorLabs, Newton, N.J.) and was determined to be 15.5 mW. After the exposure process was completed the features were developed using SU-8 developer (MicroChem Co., Newton, Mass.) for 24 hours, leaving behind the structures. The structures were truncated cones approximately 1000 microns tall.

The height of each written structure was measured using a confocal microscope (Keyence VHX-600, Keyence Co., Osaka, Japan) immediately after each sample was removed from the developer. The sample was then allowed to dry completely and then the height was measured a second time. The difference in height is listed and compared as a percentage of the original height. The difference in height before and after drying is defined here as shrinkage. Lower shrinkage was preferred.

TABLE 2

Shrinkage of Nanoparticle-loaded Photoresists

| Sample | Average Shrinkage (%) |
|---|---|
| Sample A | 2.18 |
| Sample B | 7.37 |

The reduction in shrinkage greater than 3× demonstrates the advantage of adding PMMA-tethered nanoparticles to a photoresist that must undergo long development times or that is prone to absorbing developer.

Following are exemplary embodiments of photoresists containing polymer-tethered nanoparticles according to aspects of the present invention.

Embodiment 1 is a composition comprising: a photoresist; a photoinitiator system dispersed in the photoresist; and a polymer-tethered nanoparticle dispersed in the photoresist.

Embodiment 2 is a composition according to embodiment 1, wherein the photoresist comprises a negative photoresist.

Embodiment 3 is a composition according to embodiment 1, wherein the photoinitiator system comprises a two-photon photoinitiator system.

Embodiment 4 is a composition according to embodiment 1, wherein the polymer-tethered nanoparticles comprise an acrylic polymer.

Embodiment 5 is a composition according to embodiment 4, wherein the acrylic polymer comprises poly(methyl methacrylate).

Embodiment 6 is a composition according to embodiment 5, wherein the poly(methyl methacrylate) has a weight average molecular weight of from about 9,000 to about 120,000.

Embodiment 7 is a composition according to embodiment 1, wherein the polymer-tethered nanoparticles are present in an amount of from about 20 weight percent to about 40 weight percent of the total solid weight of the composition.

Embodiment 8 is a composition according to embodiment 1, wherein the nanoparticles comprise silica.

Embodiment 9 is a method of making an article comprising: providing an unexposed composition that includes a photoresist, a photoinitiator system dispersed in the photoresist and a polymer-tethered nanoparticle dispersed in the photoresist; exposing the unexposed composition with a scanned laser beam to form exposed composition in the shape of the article; and developing the composition.

Embodiment 10 is a method of making an article according to embodiment 9, wherein the photoresist comprises a negative photoresist and the photoinitiator system comprises a two-photon photoinitiator system.

Embodiment 11 is a method of making an article according to embodiment 10, wherein the polymer-tethered nanoparticles comprise an acrylic polymer.

Embodiment 12 is a method of making an article according to embodiment 11, wherein the acrylic polymer comprises poly(methyl methacrylate).

Embodiment 13 is a method of making an article according to embodiment 9, wherein developing the composition comprises dissolving the unexposed composition in a solvent that does not significantly swell the exposed composition.

Embodiment 14 is a method of making an article according to embodiment 13, wherein the exposed composition is swelled less than about 5 volume percent during developing.

Embodiment 15 is a method of making an article according to embodiment 9, wherein the article comprises a hollow microneedle or microneedle array.

Embodiment 16 is an article comprising: a photopolymerized composition derived from a precursor composition comprising: a photoresist; a photoinitiator system dispersed in the photoresist; and a polymer-tethered nanoparticle dispersed in the photoresist.

Embodiment 17 is an article according to embodiment 16, wherein the article comprises a hollow microneedle.

Embodiment 18 is an article according to embodiment 17, wherein the microneedle shrinks less than 3% in height when saturated in cyclopentanone and then dried to remove the cyclopentanone.

Embodiment 19 is an article according to embodiment 17, wherein the microneedle is used in subcutaneous drug delivery.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows. All references cited in this disclosure are herein incorporated by reference in their entirety.

What is claimed is:

1. A composition comprising:
   a photoresist;
   a two-photon photoinitiator system dispersed in the photoresist; and
   a polymer-tethered silica nanoparticle dispersed in the photoresist, wherein the polymer-tethered silica nanoparticle comprises a covalent bond between a poly(methyl methacrylate) polymer and the silica nanoparticle, and wherein the composition is unexposed.

2. A composition according to claim 1, wherein the photoresist comprises a negative photoresist.

3. A composition according to claim 1, wherein the poly(methyl methacrylate) has a weight average molecular weight of from about 9,000 to about 120,000.

4. A composition according to claim 1, wherein the polymer-tethered nanoparticles are present in an amount of from about 20 weight percent to about 40 weight percent of the total solid weight of the composition.

5. A composition according to claim 1, wherein the nanoparticles comprise silica.

6. A method of making an article comprising:
   providing an unexposed composition that includes a photoresist, a two-photon photoinitiator system dispersed in the photoresist and a polymer-tethered silica nanoparticle dispersed in the photoresist, wherein the polymer-tethered silica nanoparticle comprises a covalent bond between a poly(methyl methacrylate) polymer and the nanoparticle;
   exposing the unexposed composition with a scanned laser beam to form an exposed composition in the shape of the article; and
   developing the composition.

7. A method of making an article according to claim 6, wherein the photoresist comprises a negative photoresist.

8. A method of making an article according to claim 6, wherein developing the composition comprises dissolving the unexposed composition in a solvent that does not significantly swell the exposed composition.

9. A method of making an article according to claim 8, wherein the exposed composition is swelled less than about 5 volume percent during developing.

10. A method of making an article according to claim 6, wherein the article comprises a hollow microneedle or microneedle array.

* * * * *